United States Patent [19]
Burgio et al.

[11] Patent Number: 5,366,489
[45] Date of Patent: Nov. 22, 1994

[54] ANESTHESIA ELECTRODE AND APPLICATOR ASSEMBLY

[75] Inventors: Paul A. Burgio, Grant Township, Washington County; Richard J. Simonsen, Maplewood, both of Minn.

[73] Assignee: Minnesota Mining and Manufacturing Company, St. Paul, Minn.

[21] Appl. No.: 193,430

[22] Filed: Feb. 8, 1994

Related U.S. Application Data

[63] Continuation-in-part of Ser. No. 71,665, Jun. 2, 1993.

[51] Int. Cl.$^5$ .............................................. A61N 1/34
[52] U.S. Cl. ..................... 607/47; 607/134; 607/148
[58] Field of Search ............... 128/639, 640, 641, 642; 607/46, 47, 134, 148, 115, 116, 149, 152, 119, 122, 129, 130, 131; 606/129; 81/77, 119, 124.4

[56] References Cited

U.S. PATENT DOCUMENTS

| | | | |
|---|---|---|---|
| 1,217,217 | 2/1917 | Reagan, Jr. | 81/77 |
| 1,256,216 | 2/1918 | Fessler | 81/119 |
| 1,285,926 | 4/1918 | Bussler | 81/119 |
| 1,924,023 | 1/1932 | Carlberg | 81/77 |
| 3,709,228 | 1/1973 | Barker | 607/148 |
| 3,741,219 | 6/1973 | Sessions | 128/417 |
| 3,977,392 | 8/1976 | Manley | 128/2.1 E |
| 4,010,758 | 3/1977 | Rockland et al. | 607/131 |
| 4,067,342 | 1/1978 | Burton | 128/418 |
| 4,121,573 | 10/1978 | Crovella et al. | 128/2.1 A |
| 4,352,359 | 10/1982 | Larimore et al. | 128/640 |
| 4,398,545 | 8/1983 | Wilson | 128/798 |
| 4,424,818 | 1/1984 | Doring et al. | 607/130 |
| 4,458,696 | 7/1984 | Larimore | 128/798 |
| 4,524,087 | 6/1985 | Engel | 427/2 |
| 4,539,996 | 9/1985 | Engel | 128/640 |
| 4,554,924 | 11/1985 | Engel | 128/640 |
| 4,643,193 | 2/1987 | DeMarzo | 128/639 |
| 4,694,835 | 9/1987 | Strand | 128/640 |
| 4,768,969 | 9/1988 | Bauer et al. | 439/260 |
| 4,782,837 | 11/1988 | Hogan | 128/421 |
| 4,784,142 | 11/1988 | Liss et al. | 128/421 |
| 4,827,932 | 5/1989 | Ideker et al. | 128/642 |
| 4,827,939 | 5/1989 | Cartmell et al. | 128/640 |
| 4,842,558 | 6/1989 | Strand | 439/863 |
| 4,848,345 | 7/1989 | Zenkich | 128/419 D |
| 4,848,348 | 7/1989 | Craighead | 128/639 |

(List continued on next page.)

FOREIGN PATENT DOCUMENTS

WO89/06554  7/1989  WIPO ........................... A61N 1/32

OTHER PUBLICATIONS

3M Health Care, Medical Specialties, Product Specification for No. 1522, Double Coated Medical Tape on Liner (Apr. 1, 1991).

(List continued on next page.)

Primary Examiner—Lee S. Cohen
Assistant Examiner—Brian M. Green
Attorney, Agent, or Firm—Gary L. Griswold; Walter N. Kirn; James D. Christoff

[57] ABSTRACT

TENS electrodes and connectors useful with such electrodes are disclosed. The electrodes include active electrodes and return electrodes having a common carrier with a field of pressure sensitive adhesive for adhering the electrode to a hand (finger or thumb) of the practitioner or an applicator. Extraoral electrodes adhere to facial skin of mammals and provide TENS treatment for intraoral-procedures. The electrodes can be single channel or dual channel to combine active electrodes and return electrodes on one electrode. The connector can be single channel or dual channel and has a ridge for projecting through the tab portion of the electrode for more secure mechanical and electrical connection. Optionally, a dual channel electrode is used in combination with an elongated applicator having a bifurcated end in order to facilitate guiding a syringe needle toward a desired injection site.

15 Claims, 5 Drawing Sheets

U.S. PATENT DOCUMENTS

| | | | |
|---|---|---|---|
| 4,848,353 | 7/1989 | Engel | 128/640 |
| 4,873,974 | 10/1989 | Hagen et al. | 128/303.13 |
| 4,924,880 | 5/1990 | O'Neill et al. | 128/787 |
| 4,945,911 | 8/1990 | Cohen et al. | 128/640 |
| 4,952,177 | 8/1990 | Drake et al. | 439/828 |
| 5,012,810 | 5/1991 | Strand et al. | 128/640 |
| 5,058,589 | 10/1991 | Ding et al. | 128/640 |
| 5,133,356 | 7/1992 | Bryan et al. | 128/640 |
| 5,143,090 | 9/1992 | Dutcher et al. | 607/130 |
| 5,150,708 | 9/1992 | Brooks | 128/419 D |
| 5,195,523 | 3/1993 | Cartmell et al. | 128/640 |
| 5,215,087 | 6/1993 | Anderson et al. | 128/640 |

OTHER PUBLICATIONS

3M Medical Specialties Product Reference Guide (Excerpts concerning No. 1522 Product) (1991).

3M 6868 Single Use Electrode Product Literature (1991).

Andersson et al., "On Acupuncture Analgesia* and the Mechanism of Pain", *Am. Journal of Chinese Medicine*, vol. 3, No. 4, pp. 311–334 (1975).

Black, R. R., "Use of transcutaneous electrical nerve stimulation in density", *JADA*, vol. 113, pp. 649–652 (Oct. 1986).

Bonner, P., "Pain Control: Dentistry's Everday Challenge", *Dentistry Today*, vol. 11, p. 70 (1992).

Hochman, R., "Neurotransmitter modulator (TENS) for control of dental operative pain", *JADA*, vol. 116, pp. 208–212 (Feb. 1988).

Mannheimer et al., *Clinical Transcutaneous Electric Nerve Stimulation*, F. A. Davis Co., pp. 352–366 (1984).

Quarnstrom Letter to Burgio dated Nov. 6, 1991.

Roth et al., "Effect of transcutaneous electrical nerve stimulation for controlling pain associated with orthodontic tooth movement", *Am. Journal of Orthodontics and Dentofacial Orthopedics*, vol. 90, No. 2, pp. 132–138 (Aug. 1986).

Schwolow et al., "Effect of transcutaneous nerve stimulation (TENS) on dental pain: comparison of psychophysical and neurophysiological data and application in dentistry", *Activ. Nerv. Sup.*, vol. 30, No. 2, pp. 129–130 (1988).

ANESTHESIA ELECTRODE AND APPLICATOR ASSEMBLY

This is a continuation-in-part application of Ser. No. 08/071,665, filed Jun. 2, 1993.

FIELD OF THE INVENTION

This invention relates to electrodes and applicators used for anesthesia.

BACKGROUND OF THE INVENTION

The treatment of intraoral conditions typically involves pain or discomfort. Since the earliest days of anesthesia, attempts have been made to minimize pain or discomfort during medical and dental procedures, including intraoral-procedures.

For purposes of this invention, "intraoral-procedures" means health care manipulations by a health care practitioner done inside the oral cavity of a mammalian patient. Nonlimiting examples of intraoral-procedures include periodontal procedures, dental procedures, oral surgery, and orthodontia.

Typically, injections of local anesthetics are employed intraorally for temporary anesthesia. But these invasive procedures produce discomfort and cause high anxiety levels in patients. There is also a delay inherent between the injection and the onset of anesthesia.

Transcutaneous electrical nerve stimulation (TENS) has been employed as a method to reduce pain or discomfort for mammalian patients. Typically, the application of a low voltage, low current electrical signal through the skin counteracts nerve stimulation indicating pain or discomfort.

TENS biomedical electrodes are well known but have not previously been widely applied to intraoral-procedures. None of the TENS biomedical electrodes for intraoral-procedures were convenient to use because these electrodes were intended to stick to the soft intraoral tissue during the intraoral procedure, particularly while a cavity was being prepared and filled with restorative material. These electrodes frequently did not maintain adhesion to soft, moist tissue during these procedures in the crowded, irrigated, saliva-filled mouth. Further, saliva or irrigating fluids can drain current away from the tooth needing pain control. Another difficulty with these electrodes was the use of a splayed wire as the electrical conductor contacting the conductive adhesive in the electrode. This splayed wire could cause unacceptably high current densities.

U.S. Pat. No. 4,782,837 (Hogan) discloses a dental analgesia method and apparatus where one TENS electrode is applied to the hand and another TENS electrode is applied to the face.

TENS biomedical electrodes have employed a delivery path for electrical signals that emphasizes the surface area of the field of conductive adhesive being greater than the surface of the electrical conductor delivering the electrical signals to the field of conductive adhesive. U.S. Pat. Nos. 4,694,835 and 4,458,696 disclose TENS electrodes where perimeter dimensions of pad portions of electrical conductors are within perimeter dimensions of contiguous fields of conductive adhesives.

Thus, the present intraoral medical practices have not found a solution to a comfortable and quick administration of anesthesia.

SUMMARY OF THE INVENTION

The present invention solves the need for a comfortable and quick administration of anesthesia.

The present invention provides a transcutaneous electrical nerve stimulation assembly that comprises an elongated applicator having a shaft and a head connected to the shaft. The assembly also includes an electrode having an electrically conductive pad portion releasably connected to the head of the applicator. A lead is electrically coupled to the pad portion, and a means is provided to releasably connect the lead to the shaft such that the lead extends along at least a portion of the length of the shaft.

The present invention also provides a transcutaneous electrical nerve stimulation assembly that comprises an elongated applicator having a shaft and a head connected to the shaft, and the head includes a bifurcated end. The bifurcated end presents a first end section, a second end section and a channel located between the first end section and the second end section. The assembly also includes an electrode releasably connected to the head. The electrode includes a first pad portion extending over the first end section, a second pad portion extending over the second end section and a notch located between the first pad portion and the second pad portion. The notch is aligned with the channel.

Another aspect of the invention relates to a transcutaneous electrical nerve stimulation applicator that comprises an elongated shaft, and an elongated neck connected to the shaft and extending at an angle relative to the longitudinal axis of the shaft. The applicator also includes a head that is connected to the shaft, and the head includes a bifurcated end.

An advantage of the present invention is that the lead is retained against the shaft of the applicator by the adhesive, and normally does not interfere with other concurrent intraoral procedures. The lead also does not normally obstruct the practitioner's view of the oral cavity, thereby providing a convenience to the user. Additionally, the channel of the bifurcated end of the applicator, being aligned with the notch between pad portions of the electrode, provides a guide for assisting the practitioner in guiding the needle during an injection. The channel and the notch increase the accuracy of placement of the injection and enable the practitioner to avoid using his or her fingers to guide the needle, so that inadvertent puncture or other injury of the practitioner's hand from the needle can be avoided.

A feature of the present invention is that perimeter dimensions of the electrically conductive surface are at least equal to and preferably greater than the perimeter dimensions of the field of conductive adhesive receiving the TENS electrical signals from the electrical conductor.

Another feature of the present invention is the maintenance of relative uniform current densities during TENS oral administration without significant areas of high and low current density.

The present invention also solves an unexpected problem associated with the dimensions of the perimeter of a field of conductive adhesive relative to the perimeter dimensions of the electrical conductor delivering electrical signals to that field of conductive adhesive. This problem is one of current density. Since current density decreases significantly when traveling transversely even several millimeters through a field of conductive adhesive, it has been found in the present invention that it is important that the distance traveled by the current be minimized. The electrodes of the present invention minimize the distance traveled by the current to only a few millimeters or less of the thickness of the field of conductive adhesive.

In the present invention, the current density of TENS administration is substantially uniform due to the construction of the electrode such that the perimeter of the electrically conductive surface is beyond the perimeter of the field of conductive adhesive which the conductor contacts. Thus, the maximum distance through which current must travel is through the thickness of the conductive adhesive between the electrically conductive surface and mammalian skin.

Embodiments of the invention are described with reference to the following drawings.

EMBODIMENTS OF THE INVENTION

Figure 1:
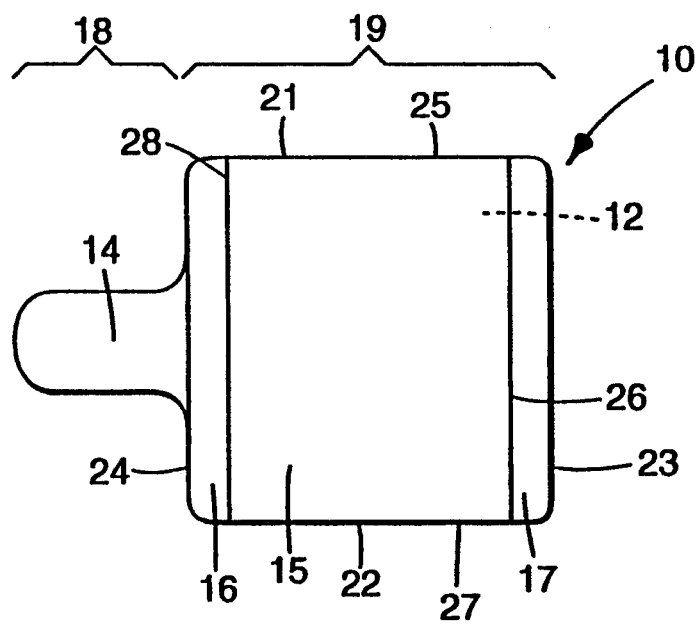
FIG. 1 is a bottom plan view of a TENS electrode according to the present invention.
Figure 2:
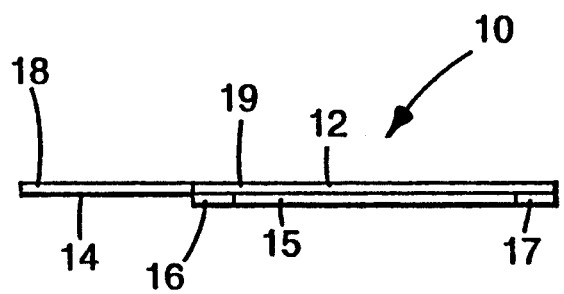
FIG. 2 is a side plan view of the TENS electrode of FIG. 1.

FIGS. 1 and 2 are bottom and side plan views, respectively, of one embodiment of an intraoral-procedures TENS electrode 10 of the present invention. From the surface farthest away from mammalian skin, electrode 10 comprises a non-conductive flexible backing 12 having an electrically conductive surface 14 contacting both a field 15 of conductive adhesive and two opposing fields 16 and 17 of biocompatible pressure sensitive skin adhesive. Not shown is a release liner that contacts fields 15, 16, and 17 of adhesive when electrode 10 is not in use.

Flexible backing 12 comprises a tab portion 18 and a pad portion 19. Both tab portion 18 and pad portion 19 have electrically conductive surface 14, but field 15 of conductive adhesive contacts only pad portion 19. Tab portion 18 is suitable for releasable attachment to a electrical connector that delivers the TENS administration.

Pad portion 19 has a perimeter defined by edges 21, 22, 23, and 24. By comparison, field 15 of conductive adhesive has a perimeter defined by edges 25, 26, 27, and 28. The surface area of field 15 of conductive adhesive within edges 25–28 contacts the surface area of pad portion 19 within edges 21–24 of pad portion 19, such that the surface area of the pad portion of electrically conductive surface 14 is equal to or greater than the surface area of field 15 of conductive adhesive and such that the perimeter dimensions of the field 15 of conductive adhesive are within the perimeter dimensions of the pad portion 19 of the electrical conductive surface.

The significance of the perimeter dimensions of electrically conductive surface 14 relative to field 15 of conductive adhesive has been previously summarized in the features of the invention. A substantially uniform current density has been achieved by electrode 10 of the present invention because, while field 15 of conductive adhesive is conductive, it is also more resistant to transmission of electrical signals to mammalian skin than electrically conductive surface 14. Based on the principles of Ohm's Law, the preferred delivery of TENS treatment to mammalian skin should be the path of least resistance. Constructing electrode 10 such that the maximum delivery path for TENS electrical signals is the thickness of the field 15 of conductive adhesive minimizes the resistance encountered in the delivery of TENS treatment.

Thus, a TENS electrode of the prior art with perimeter dimensions of conductive adhesive exceeding perimeter dimensions of an electrical conductor contacting that conductive adhesive provides an unwanted high current density in a narrow region of the surface area of the electrode, causing uncomfortable sensations during TENS administration. The undesirable high peak of current density could cause such pain for the mammalian patient as to challenge the pain of intraoral-procedures itself.

Fields 16 and 17 of biocompatible skin adhesive are not ionically conductive as is field 15 but are preferably at opposing locations to assist in the maintenance of adhesive contact of electrode 10 to skin of a mammalian patient. The opposing locations proximal and distal to tab portion 18 provide a relatively high level of adhesion to mammalian facial skin. In several mammalian species facial skin (as opposed to non-facial skin) has a high concentration of oil secreting glands that can disrupt continued adhesion of electrode 10. Since during TENS administration, mammalian patients can perceive that electrode 10 is becoming dislodged, assurance of adhesion of electrode 10 to the face throughout the intraoral procedure is important.

Unlike TENS electrodes of the prior art, use of two electrodes 10 can be adhered to a mammalian face to assist intraoral-procedures. Unexpectedly, location of electrodes 10 as an active electrode and a return electrode both extraorally on the face of a patient can provide pain relief intraorally within the jaw and mouth of the patient. While the principles are not completely understood, and not being limited to any particular theory, using two electrodes 10 can provide effective pain relief during intraoral-procedures.

Selection of materials to construct electrode 10 are known to those skilled in the art of biomedical electrode construction. U.S. Pats. Nos. 4,352,359 (Larimore); 4,524,087 (Engel); 4,539,996 (Engel); 4,554,924 (Engel); 4,848,348 (Carim); 4,848,353 (Engel); 5,012,810 (Strand et al.); 5,133,356 (Bryan et al.); co-pending and co-assigned U.S. patent application Ser. No. 07/686,049 (Anderson et al.); co-pending and co-assigned U.S. patent application Ser. No. 07/792,442 (Duan et al.); and co-pending and co-assigned U.S. patent application Ser. No. 07/792,957 (Uy et al.) all describe suitable materials for the construction of biomedical electrodes useful for TENS treatment, and all are incorporated by reference as if fully rewritten herein.

Of the numerous electrically nonconductive materials known to those skilled in the art, presently preferred for backing material 12 are polyester films of about 0.01 mm thickness commercially available as "Melinex" branded films (e.g., 329 and 339) from ICI Americas of Hopewell, Va. Preferably, the film can be treated with a corona treatment to improve the adhesion of the electrically conductive surface to the backing material.

Of the numerous electrically conductive materials known to those skilled in the art, inks containing electrical conductive particles such as graphite or metals are useful with metal-containing inks being preferred. Presently preferred for electrically conductive surface 14 is a silver loaded ink "N-30" ink or a silver/silver chloride "R-300" ink, both commercially available from Ercon, Inc. of Waltham, Mass.

Of the numerous conductive adhesives known to those skilled in the art, presently preferred for field 15 of conductive adhesive are those conductive adhesives as described in the table at Column 16 of U.S. Pat. No. 5,012,810 (Strand et al.) and as disclosed in U.S. Pat. Nos. 4,524,087; 4,539,996; 4,848,353; and 4,554,924 (all Engel); co-pending and co-assigned U.S. patent application Ser. No. 07/792,442 (Duan et al.); and co-pending and co-assigned U.S. patent application Ser. No. 07/792,957 (Uy et al.). Presently preferred for field 15 of conductive adhesive is an acrylic acid/N-vinyl-pyrrolidone copolymer plasticized with glycerol prepared according to the disclosure of U.S. Pat. No. 4,848,353 (Engel), which is incorporated by reference herein. The adhesive preferably comprises about 10 weight percent acrylic acid monomer, about 10 weight percent N-vinyl-pyrrolidone, about 51 weight percent glycerol, about 0.12 weight percent guar gum, about 3 weight percent sodium hydroxide, about 25 weight percent water, about 0.07 weight percent benzildimethylketal photoinitiator, and about 0.12 weight percent triethylene-glycol-bis-methacrylate chemical crosslinker prepared according to Example 1 of U.S. Pat. No. 4,848,353.

Of the numerous biocompatible skin adhesives known to those skilled in the art, presently preferred for fields 16 and 17 of adhesive are acrylate pressure sensitive adhesives. Acrylate ester copolymer adhesives are particularly preferred. Such materials are generally described in U.S. Pat. Nos. 2,973,286; Re 24,906; Re 33,353; 3,389,827; 4,112,213; 4,310,509; 4,323,557; 4,732,808; 4,917,928; 4,917,929; and European Patent Publication 0 051 935, all incorporated herein by reference. Presently preferred is a pressure sensitive adhesive tape commercially available as No. 1522 pressure sensitive medical tape from the Medical Specialties Department of the Consumer and Professional Health Care Division of Minnesota Mining and Manufacturing Company of St. Paul, Minn.

Figure 3:
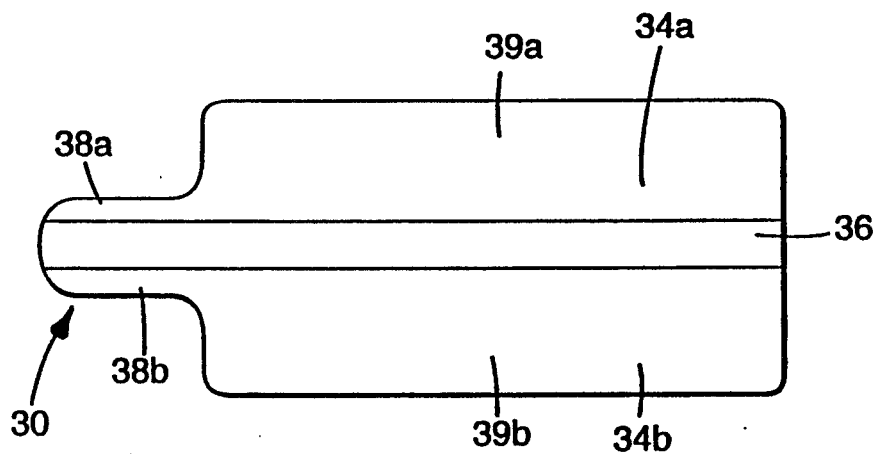
FIG. 3 is a modified bottom plan view of an alternative embodiment of the present invention having two TENS channels of stimulation.
Figure 4:
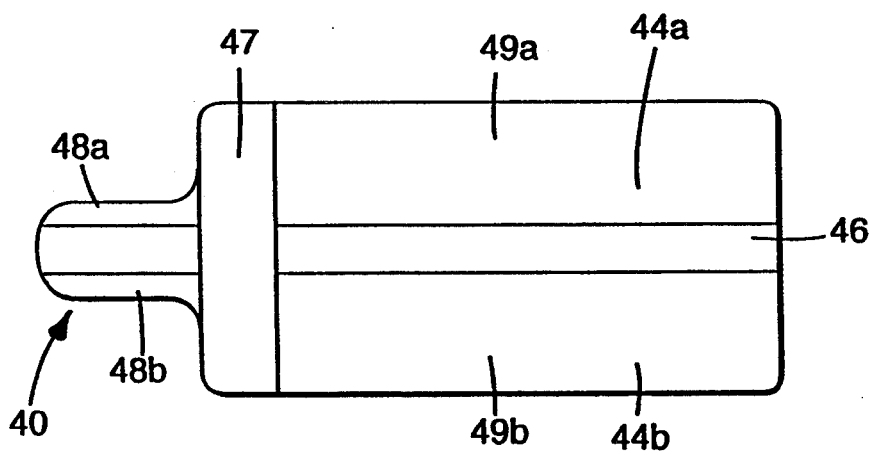
FIG. 4 is a bottom plan view of an alternative embodiment to the embodiment of FIG. 3.
Figure 5:
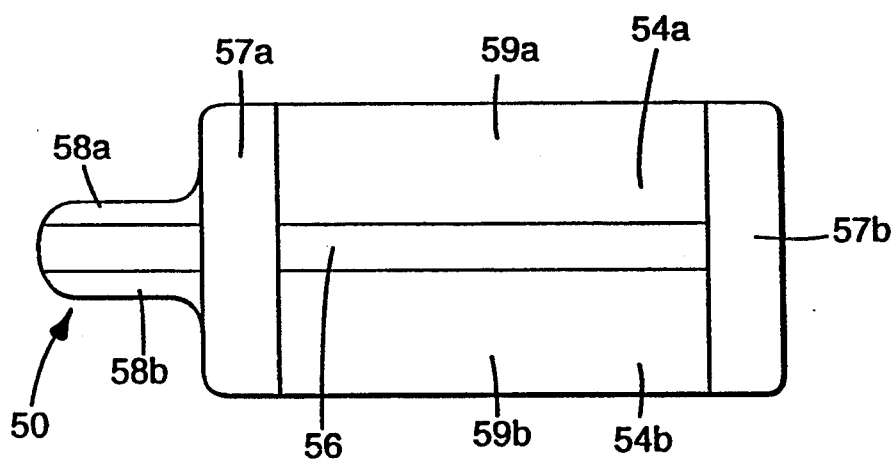
FIG. 5 is a bottom plan view of an alternative embodiment to the embodiment of FIG. 3.

Now referring to FIGS. 3–5, bottom plan views (as modified with fields of adhesive removed), three alternative embodiments of the present invention having two TENS channels of intraoral stimulation are described. Electrodes 30, 40, and 50 each differ from electrode 10 previously described in that there are two channels of TENS adminstration created by electrically conductive surfaces 34a, 44a, 54a, respectively, for one channel and electrically conductive surfaces 34b, 44b, and 54b, respectively, for the second channel. Thus, tab portions 38a, 48a, and 58a, respectively, and pad portions 39a, 49a, and 59a, respectively, connect to one channel, while tab portions 38b, 48b, and 58b, respectively, and pad portions 39b, 49b, and 59b connect to a second channel.

The embodiments of FIGS. 3–5 differ based on the placement of fields of biocompatible skin adhesive. In FIG. 3, a single strip 36 of biocompatible skin adhesive bisects the electrically conductive surfaces 34a and 34b. Fields of conductive adhesive (not shown) reside in contact with the surfaces 34a and 34b. In FIG. 4, strip 46 corresponds to strip 36 in FIG. 3, and electrode 40 further has a strip 47 of biocompatible skin adhesive proximal to tab portions 48a and 48b for greater assurance of adhesion during TENS treatment. FIG. 5 also shows the separation of channels between pad portions 59a and 59b using strip 56. Opposing strips 57a and 57b of biocompatible skin adhesive in FIG. 5 correspond to fields 16 and 17 of adhesive shown in FIGS. 1 and 2.

In each embodiment of FIGS. 3–5, the principle of the invention of perimeter dimensions is retained. Indeed, the total of the conductive adhesive surface areas is less than the total of the electrically conductive surfaces' areas, and the surface area of each respective field of conductive adhesive is no greater than the surface area of its respective pad portions 39a, 39b, 49a, 49b, 59a, or 59b. Further, each field of conductive adhesive has a perimeter dimension within the perimeter dimension of its respective pad portions 39a, 39b, 49a, 49b, 59a, or 59b.

Electrodes 30, 40, and 50 can be constructed from materials selected by those skilled in the art in a similar manner to those selected for electrode 10. Preferred materials for each component described for electrode 10 apply also to electrodes 30, 40, and 50.

Electrodes 30, 40, and 50 are advantageous because only one medical device is employed for two purposes. Traditionally, two devices have been required, one for each electrode purpose. Electrodes 30, 40, and 50, each having two channels of TENS administration, provide a time-savings and convenience to the health care provider while reducing cost since only one dual channel connector is required. Further, for the mammalian patient, less facial tissue is being stimulated using one dual channel electrode than if two single channel electrodes were used. With less facial tissue being stimulated, the mammalian patient generally experiences fewer tingling sensations, increasing comfort and augmenting pain control during the intraoral procedure.

Figure 6:
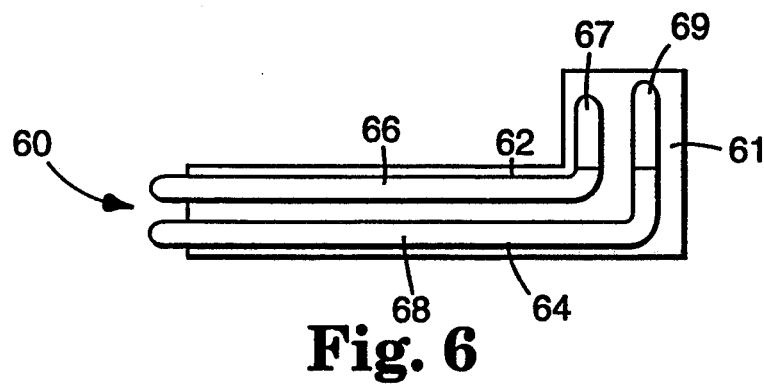
FIG. 6 is a bottom plan view of an intraoral TENS electrode of the present invention.
Figure 7:
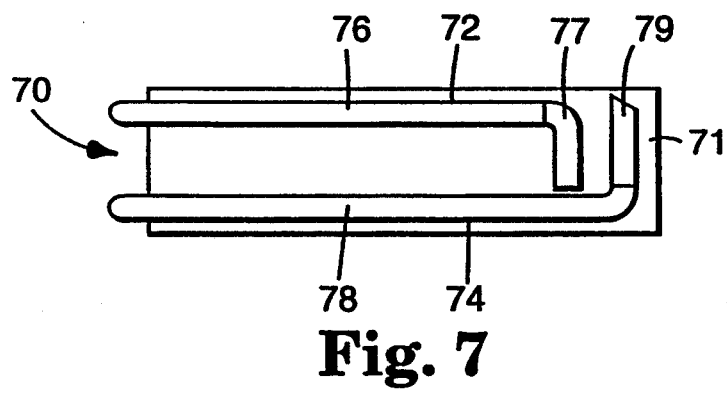
FIG. 7 is a bottom plan view of an alternative embodiment of an intraoral TENS electrode of FIG. 6.
Figure 8:
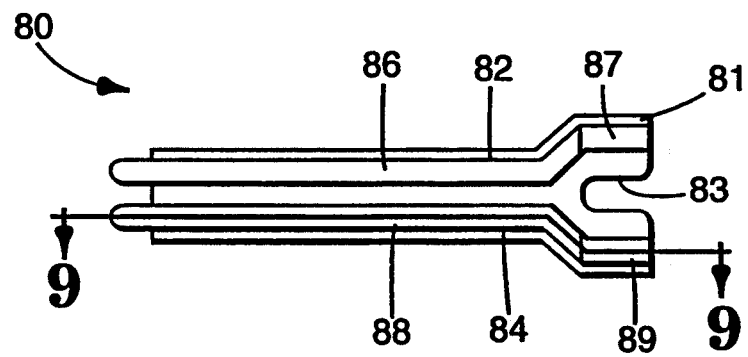
FIG. 8 is a bottom plan view of an alternative embodiment of an intraoral TENS electrode of FIG. 6.

Now referring to FIGS. 6–8, all bottom plan views, three alternative embodiments of intraoral TENS electrodes of the present invention are described. Like electrodes 30, 40, and 50, these electrodes 60, 70, and 80 each have two channels, an active channel and a return channel. Unlike electrodes 30, 40, and 50, electrodes 60, 70, and 80 are designed for intraoral TENS administration.

These embodiments of the present invention provide intraoral TENS electrodes 60, 70, and 80, each comprising at least one active electrode pad 62, 72, and 82, respectively, and at least one return electrode pad 64, 74, and 84, respectively, integrally joined to a common carrier, 61, 71, and 81, respectively. Each electrode pad 62, 64, 72, 74, 82, and 84 has a tab portion 66, 68, 76, 78, 86, and 88, respectively, and a pad portion 67, 69, 77, 79, 87, and 89, respectively, such that each tab portion has sufficient length to extend extraorally. Optionally, the common carrier is a backing material having a pressure sensitive adhesive thereon. Typically the common carrier is useful for adhesion to the gloved hand of a dental or oral practitioner for placing the TENS electrode intraorally.

Of the three embodiments, electrode 80 is preferred. Optionally, electrode 80 has a notch 83 in common carrier 81 between pads 82 and 84 to permit alignment of electrode adjacent to an injection site, preferably within notch 83.

Electrodes 60, 70, and 80 need not have both the active and return pads mounted on a common carrier. Electrodes 60, 70, and 80 can be split along the long axis to provide a separation of active and return TENS administration sites, including placement of either the active pad or the return pad intraorally and the other extraorally, or the placement of both pads intraorally in separate locations. In these embodiments, presence of the pressure sensitive adhesive on the backing material facilitates separated placement of the pads in adjustable locations for comfort and effectiveness.

Figure 9:
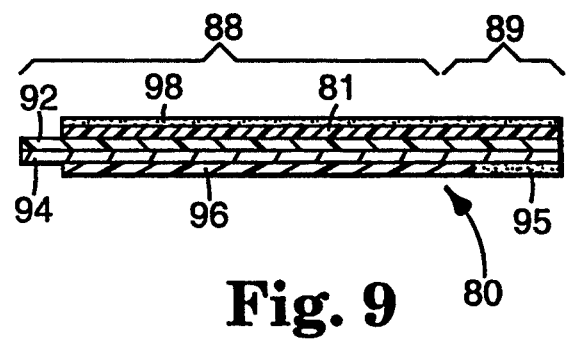
FIG. 9 is a sectional view of an alternative embodiment of the intraoral TENS electrode of FIG. 8 taken along lines 9—9.

Referring to FIG. 9, a sectional view of the embodiment of FIG. 8 along lines 9—9 is shown for pad 84, although the sectional view also demonstrates the construction of pad 82 as well as the embodiments of FIGS. 6 and 7. Pad 84 of electrode 80 has a flexible backing 92 comprising a tab portion 88 and a pad portion 89 and is adhered to common carrier 81. Both tab portion 88 and pad portion 89 have electrically conductive surfaces 94, but field 95 of conductive adhesive contacts only pad portion 89. Tab portion 88 is suitable for releasable attachment to an electrical connector that delivers the TENS administration. Covering field 95 at portions other than the distal end of pad 84 is a non-conductive layer 96 such as a single-coated pressure sensitive medical tape, so that field 95 only resides at the distal end of electrode pad 84. Covering common carrier 81 is a field of biocompatible pressure sensitive adhesive 98 to permit pad 84 to be adhered to glove or hand of a health care practitioner, or an applicator, for intraoral placement of electrode 80. Alternatively, field 95 has sufficient adhesiveness to permit electrode 80 to adhere to less moist portions of the intraoral cavity, such as the soft palette.

Pad portion 89 has perimeter dimensions that at least exceed perimeter dimensions of field 95 in accordance with the principles of the present invention as described with respect to electrode 10 above.

Electrodes 60, 70, and 80 can be constructed from materials selected by those skilled in the art in a similar manner to those selected for electrode 10, with the addition of non-conductive layer 96 being constructed from a single-coated pressure sensitive medical tape commercially available as No. 1525L medical tape from the Medical Specialties Department of the Consumer and Professional Health Care Division of Minnesota Mining and Manufacturing Company, and the addition of field 98 being constructed from a double-coated pressure sensitive medical tape such as No. 1522 tape described above. Preferred materials for each component described for electrode 10 apply also to electrodes 60, 70, and 80.

Figure 10:
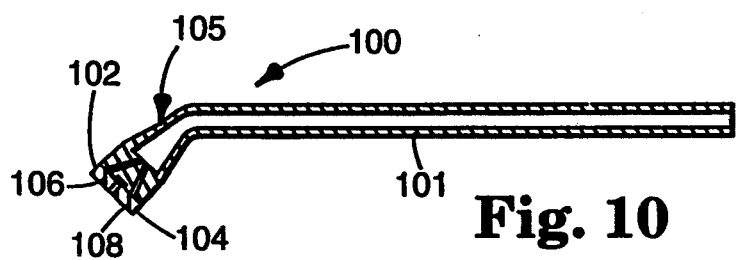
FIG. 10 is a cross-sectional view of an alternative embodiment of an intraoral TENS electrode of FIG. 6 in conjunction with an instrument to assist placement of the TENS electrode intraorally.

Referring to FIG. 10, which is a cross-sectional view of an alternative embodiment of an intraoral TENS electrode of FIG. 8 in conjunction with an instrument to assist placement of the TENS electrode intraorally. Electrode 100 is adhered to a shaft 101 providing support for both active electrode pad 102 and return electrode pad 104 with pad portions 106 and 108, respectively, extending from head 105 at the end of shaft 101. The arrangement of active electrode pad and return electrode pad to head 105 is similar to the arrangement of electrode 80. Optionally on the surface of head 105 (not shown) is a field of conductive adhesive that assists in the intraoral delivery of TENS treatment.

Selection of materials for the various components of electrode 100 can be made from materials known to those skilled in the art.

Shaft 101 can be made from autoclavable polymers such as acrylonitrile-butadiene-stryene (ABS), polycarbonate, polysulfone, polyethersulfone, or polyetherimide polymers. Presently preferred polymers are injection-molded polyetherimide or polyethersulfone polymers. Electrode pads 102 and 104 can be made from the same materials as employed for electrodes 10, 30, 40, and 50. Head 105 can be made from the same material as shaft 101. The field of pressure sensitive adhesive can be made from the same pressure sensitive adhesives as employed in electrodes 10, 30, 40, or 50. The field of conductive adhesive can be made from the same conductive adhesives as employed in electrodes 10, 30, 40, and 50.

Features of intraoral electrodes of the present invention include the following. Active and return electrode pads are parallel and in the same plane. Active and return electrode pads are attached to a common carrier, preferably in a shaft such as shaft 101 terminating at a head such as head 105. The pad portions are leads that are an integral part of the electrode pads and extend extraorally to connect to the electrical stimulation unit. The integral electrode pads and leads have an adhesive thereon that can adhere to a gloved hand or to the surface of the head of an instrument, making the electrode a disposable item while permitting reuse of the head and shaft after sterilization. The pad can deliver TENS treatment through the pad portions at the exposed surface of the head, either through a conductive adhesive or without a conductive adhesive. The active and return electrode pads are configured as shown in FIGS. 6–8 for maximum uniform pain control at the treatment site. A single electrode connector of the present invention described below can be used to connect the intraoral electrode to the TENS stimulation unit, which minimizes the number of connections and wires in and about the oral cavity during intraoral-procedures.

Figure 11:
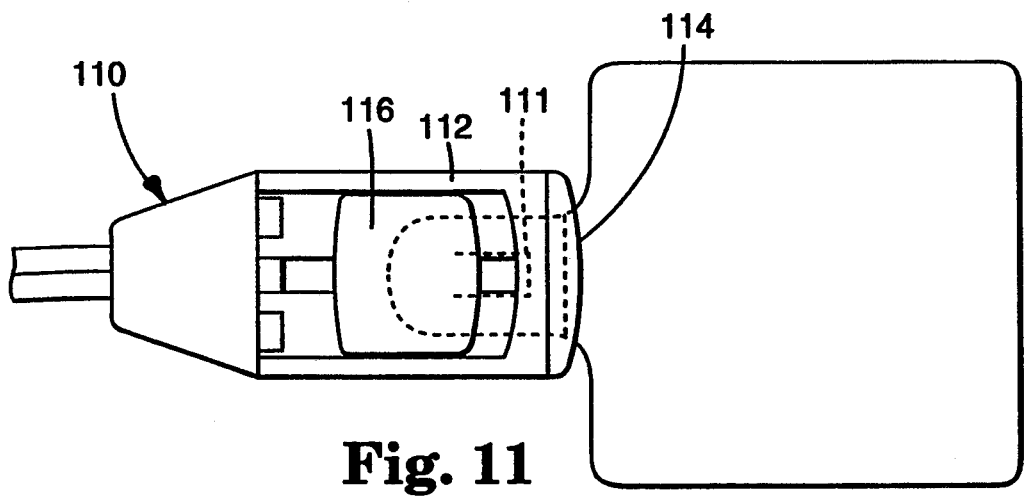
FIG. 11 is a top plan view of a connector of the present invention as used with a TENS electrode of the present invention.
Figure 12:
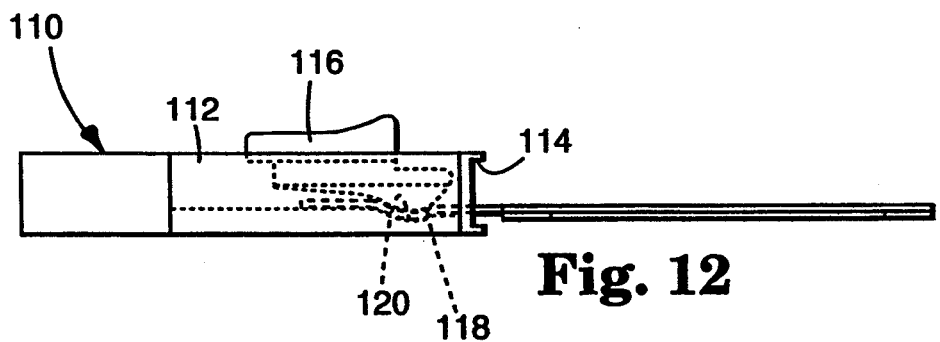
FIG. 12 is a side plan view of the connector of FIG. 11.

Now referring to FIGS. 11 and 12, top and side plan views, respectively, of a connector of the present invention for use with a TENS electrode of the present invention is described. All electrodes 10, 30, 40, 50, 60, 70, 80, and 100 require firm and unmistakable engagement with the electrical stimulation unit to maintain electrical connection for TENS treatment and continued anesthesia during intraoral-procedures. The respective tab portions of the electrodes are particularly suited for connectors that surround the tab portions and firmly and electrically contact the electrically conductive surfaces of such tab portions.

To assure mechanical connection with connector 110, the respective tab portions of the electrodes of the present invention can be modified to provide a slot opening 111, cut on two, three, or four sides, for mechanical engagement of connector 110 when electrical connection is desired.

Connector 110 improves upon a connector shown and described in U.S. Pat. No. 4,842,558 (Strand), the disclosure of which is incorporated by reference herein. Connector 110 has a housing 112 having an opening 114 for insertion of each tab, a slide 116 moveable within the housing to contact a slot opening 111 in an electrode tab portion, a ridge 118 extending from the slide to extend through the slot opening 111 of the tab at the point of contact with the tab, and a receptacle 120 in the housing 112 for receiving the ridge after ridge 118 has been moved to a position where it is extending through the tab.

Slot opening 111 in the tab portion can be completely open with the cut portion (slot portion of the backing) removed or the slot portion can be cut on three sides. In the latter instance, slot opening 111 would be pushed by ridge 118 on slide 116 into the corresponding receptacle 120. In either instance, the tab portion of an electrode of the present invention would be securely held in the connector 110.

Figure 13:
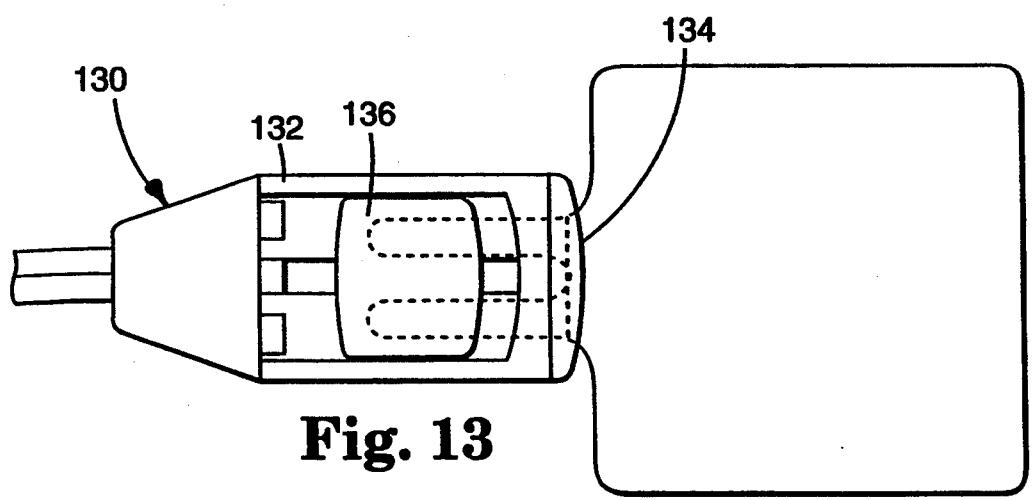
FIG. 13 is a top plan view of a connector of the present invention as used with a two channel TENS electrode of the present invention.

Electrodes 30, 40, 50, 60, 70, 80, and 100 each comprise both an active electrode channel and a return electrode channel. The proximity of the two channels on one electrode permits a single connector to be employed according to the present invention. FIG. 13 shows a top plan view of an alternate embodiment of a connector of the present invention. Connector 130 differs from connector 110, in that connector 130 has two channels corresponding to the two channels of electrodes 30, 40, 50, 60, 70, 80, and 100. Connector 130 has two electrical pathways within housing 132 such that two electrical pathways on slide 136 electrically and mechanically contact corresponding channels through opening 134 on electrode tab portions. Use of connector 130 allows one connector to attach to a single electrode yet provides the requisite two channels for TENS administration.

Figure 14:
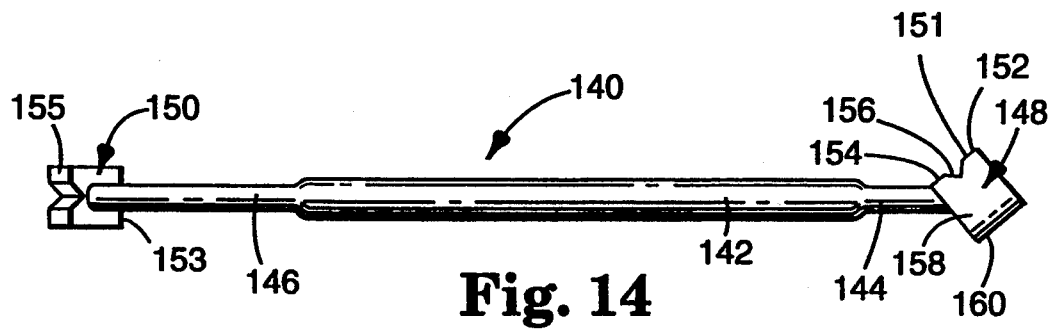
FIG. 14 is a top plan view of a TENS applicator of the present invention.
Figure 15:
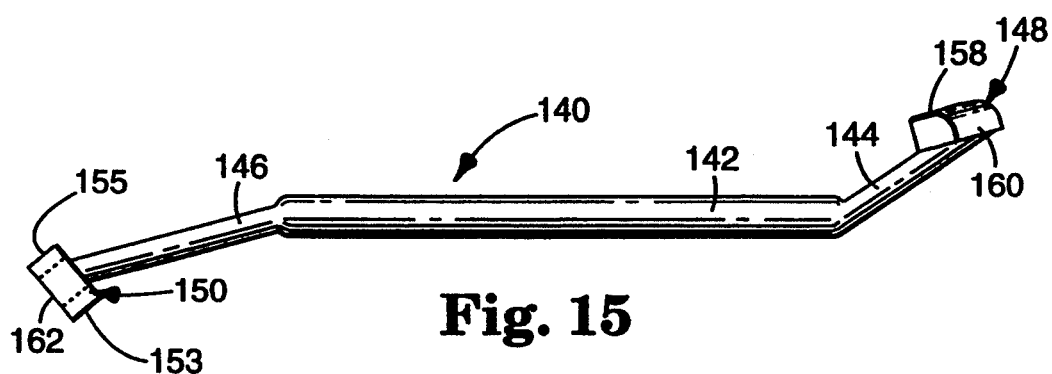
FIG. 15 is a side plan view of the applicator of FIG. 14.
Figure 16:
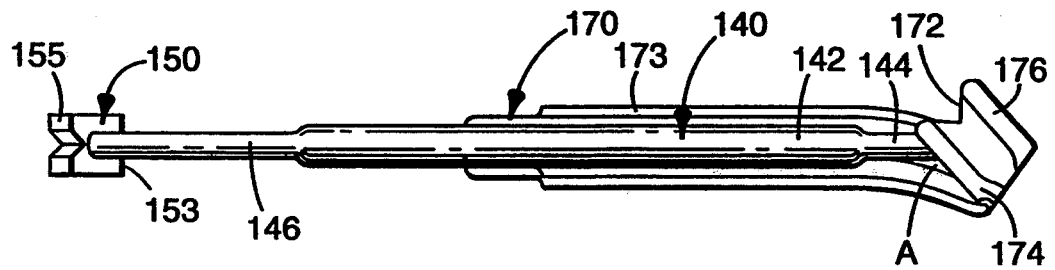
FIG. 16 is a top plan view of the applicator illustrated in FIGS. 14–15, along with a TENS electrode of the present invention.

An elongated applicator 140 as shown in FIGS. 14–16 has an elongated, cylindrical shaft 142. One end of the shaft 142 is integrally connected to a first cylindrical neck 144, while the opposite end of the shaft 142 is integrally connected to a second cylindrical neck 146. Both of the necks 144, 146 extend at an angle relative to the longitudinal axis of the shaft 142. The first neck 144 is integrally connected at its outer end to a first head 148, while the second neck 146 is integrally connected at its outer end to a second head 150.

As illustrated in FIG. 14, the first head 148 includes a bifurcated end 151 that presents a first end section 152, a second end section 154 and a generally V-shaped channel 156 located between the spaced apart end sections 152, 154. An outer wall 158 of the first head 148 extends away from the end sections 152, 154 in a flat plane, and is integrally joined to a curved wall that presents a second end 160 opposite the bifurcated end 151.

The second head 150 of the applicator 140 has a first bifurcated end 153 similar to the first bifurcated end 151 of the head 148. The first bifurcated end 153 is located on its outermost end of the second head 150 (i.e., the end of the second head 150 remote from the second neck 146). The second head 150 also has an outer wall 162 that extends in a flat plane from the first bifurcated end 153 to a second bifurcated end 155 located next to the neck 146.

The applicator 140 can be made of the same materials as mentioned earlier in connection with shaft 101 illustrated in FIG. 10. Preferably, the applicator 140 is integrally molded of a clear, translucent or opaque aromatic liquid crystal polyester such as VECTRA A530 (from Hoechst-Celanese); an alternative material is an acetal resin such as DELRIN (from E.I. dupont de Nemours & Co.). The applicator is sterilized by cold sterilization or by an autoclave process.

FIG. 16 depicts an intraoral-procedures TENS assembly that comprises the applicator 140 along with an intraoral electrode 170. Electrode 170 is substantially the same as electrode 80 described above in connection with FIGS. 8 and 9, and as a consequence a detailed description of each element of the electrode will not be repeated.

Biocompatible pressure sensitive adhesive 173 (similar to adhesive 98), covers a common carrier and provides a means to releasably connect the electrode 170 to shaft 142 as well as to the outer wall 158 of the first head 148. Typically, the electrode 170 is spaced from the neck 144 at the location marked "A" in FIG. 16 as it extends about neck 144, to facilitate flat, firm contact of the electrode 170 with both the outer wall 158 of the first head 148 as well as with the side of the applicator shaft 142 that is remote from the first head 148. Other connecting means are also possible, such as a mechanical clip or interlocking structure.

Figure 17:
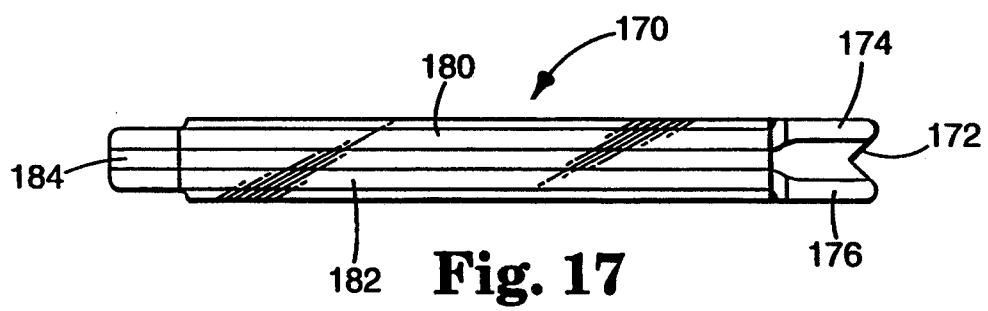
FIG. 17 is a bottom plan view of the TENS electrode alone that is shown in FIG. 16.

As shown in FIGS. 16–17, a notch 172 of the electrode 170 is located between a first pad portion 174 and a second pad portion 176. Preferably, the notch 172 is aligned with the channel 156 when the applicator 140 and the electrode 170 are assembled together. Such alignment facilitates use of the channel 156 and the notch 172 as guides to assist in alignment of the electrode 170 to a particular location in the oral cavity. For example, the needle of a syringe containing an anesthetic may be guided by the channel 156 and the notch 172 toward an injection site in the oral cavity that is directly between the pad portions 174, 176.

Advantageously, adhesive 173 retains the electrode 170 in place against the applicator 140, such that electrode 170 does not normally obstruct the view of the practitioner toward the injection site. In this regard, the applicator 140 together with the electrode 170 can be oriented as desired in the oral cavity in such a manner as may be most useful for the situation at hand.

The electrode 170 may be connected to the applicator 140 in a variety of different configurations, and the illustration in FIG. 16 shows only one example. As an alternative, the orientation of electrode 170 may be reversed such that the notch 172 is in alignment with the channel of the first bifurcated end 153 of the second head 150. As another alternative, the pad portions 174, 176 may be placed on the second head 150 in such an orientation that the notch 172 is in alignment with the channel of the second birfurcated end 155 of second head 150. The larger head 148 is useful for placement of the pad portions 174, 176 on the maxillary incisive papilla, while the smaller head 150 is useful for placing the pad portions 174, 176 in remaining areas of the patient's oral cavity.

Electrode 170 has tab portions 180, 182 (FIG. 17) that are leads and that are an integral part of the electrode portions 176, 174 respectively. FIG. 17 also illustrates a flexible backing (similar to backing 92) upon which the pad portions 174, 176, tab portions 180, 182 as well as the common carrier are mounted. A field of conductive adhesive (similar to field 95) covers the pad portions 174, 176.

Preferably, the areas of the outer walls 158, 162 are each equal to or slightly smaller than the area of the electrode 170 adjacent pad portions 174, 176. Optionally, the electrode 170 overhangs the bifurcated end of the adjacent applicator head by a distance of 2 to 4 mm, to facilitate conforming the shape of pad portions 174, 176 to the patient's tissue or skin in regions where the tissue or skin is curved.

The invention shown in FIG. 16 is especially useful for dental or medical procedures where local anesthesia is needed for only a relatively short time. Examples include injections, tooth extractions, or tooth restorative procedures. Applicator 140 could be held by the practitioner, or optionally by the patient. When the assembly shown in FIG. 16 is used intraorally, tab portions 180, 182 and applicator shaft 142 are of lengths sufficient to extend extraorally when the pad portions 174, 176 are in place in the oral cavity.

Various embodiments of the invention have been described. The following claims and their equivalents provide a complete understanding of the present invention.

What is claimed is:

1. A transcutaneous electrical nerve stimulation assembly comprising:
    an elongated applicator having a shaft with an external surface and a head connected to said shaft;
    an electrode having an electrically conductive pad portion releasably connected to said head of said applicator;
    a lead electrically coupled to said pad portion; and
    an adhesive releasably connecting said lead to said external surface of said shaft such that said lead extends along at least a portion of the length of said shaft.

2. The assembly of claim 1, wherein said electrode includes a carrier, and wherein said lead and said pad portion are located on said carrier.

3. The assembly of claim 2, wherein said carrier extends along at least a portion of said shaft and also extends across at least a portion of said head.

4. The assembly of claim 2, wherein said adhesive is a pressure sensitive adhesive located on said carrier.

5. A transcutaneous electrical nerve stimulation assembly comprising:.
    an elongated applicator having a shaft with an external surface and a head connected to said shaft;
    an electrode having an electrically conductive pad portion releasably connected to said head of said applicator;
    a lead electrically coupled to said pad portion; and
    means for connecting said lead to said external surface of said shaft such that said lead extends along at least a portion of the length of said shaft,
    wherein said electrode includes a second electrically conductive pad portion releasably connected to said head.

6. A transcutaneous electrical nerve stimulation assembly comprising:
    an elongated applicator having a shaft and a head connected to said shaft, said head including a bifurcated end presenting a first end section, a second end section and a channel located between said first end section and said second end section; and
    an electrode releasably connected to said head, said electrode including a first pad portion extending over said first end section, a second pad portion extending over said second end section and a notch located between said first pad portion and said second pad portion, said notch being generally aligned with said channel.

7. The assembly of claim 6, wherein said assembly includes an adhesive releasably connecting said electrode to said head.

8. The assembly of claim 6, wherein said electrode includes a carrier, a first lead electrically coupled to said first pad portion and a second lead electrically coupled to said second pad portion, and wherein said first lead, said second lead, said first pad portion and said second pad portion are located on said carrier.

9. The assembly of claim 8, wherein said carrier includes an adhesive releasably connecting said electrode to said applicator.

10. The assembly of claim 9, wherein said carrier extends along at least a portion of said shaft.

11. The assembly of claim 6, wherein said applicator includes a second head connected to said shaft.

12. The assembly of claim 6, wherein said assembly includes a first lead connected to said first pad portion and a second lead connected to said second pad portion, and wherein said first lead and said second lead are adhesively connected to said shaft.

13. The assembly of claim 6, wherein said head includes an outer wall in contact with said first pad portion and said second pad portion, and wherein said first pad portion and said second pad portion collectively extend over substantially the entire extent of said wall.

14. The assembly of claim 6, wherein said head includes an outer wall connected to said first pad portion and said second pad portion, and wherein said first pad portion and said second pad portion extend beyond said wall.

15. The assembly of claim 6, wherein said shaft has a certain cross-sectional area in longitudinally transverse directions, and wherein said head includes an outer wall connected to said first pad portion and said second pad portion, and wherein said outer wall has an area larger than the said cross-sectional area of said shaft.

* * * * *